(12) United States Patent
Boote (10) Patent No.: US 9,764,533 B2
(45) Date of Patent: Sep. 19, 2017

(54) GLAZING

(71) Applicant: PILKINGTON GROUP LIMITED, Lancashire (GB)

(72) Inventor: Joseph Jeremy Boote, Lancashire (GB)

(73) Assignee: PILKINGTON GROUP LIMITED, Lancashire (GB)

( * ) Notice: Subject to any disclaimer, the term of this patent is extended or adjusted under 35 U.S.C. 154(b) by 0 days.

(21) Appl. No.: 14/894,788

(22) PCT Filed: May 29, 2014

(86) PCT No.: PCT/GB2014/051630
§ 371 (c)(1),
(2) Date: Nov. 30, 2015

(87) PCT Pub. No.: WO2014/191743
PCT Pub. Date: Dec. 4, 2014

(65) Prior Publication Data
US 2016/0101603 A1    Apr. 14, 2016

(30) Foreign Application Priority Data

May 29, 2013 (GB) .................................. 1309549.2

(51) Int. Cl.
*G01R 27/02* (2006.01)
*B32B 17/10* (2006.01)
(Continued)

(52) U.S. Cl.
CPC .. *B32B 17/10394* (2013.01); *B32B 17/10036* (2013.01); *B32B 17/10761* (2013.01); *G01N 27/00* (2013.01); *G08B 13/04* (2013.01)

(58) Field of Classification Search
CPC ........... G01R 27/02; G01R 27/26; G01R 1/30
See application file for complete search history.

(56) References Cited

U.S. PATENT DOCUMENTS 4,565,919 A    1/1986 Bitter et al.
4,829,163 A    5/1989 Rausch et al.
(Continued)

FOREIGN PATENT DOCUMENTS

DE    28 09 436 A1    9/1979
DE    93 03 273 U1    7/1993
(Continued)

OTHER PUBLICATIONS

International Search Report (PCT/ISA/210) issued on Sep. 1, 2014, by the European Patent Office as the International Searching Authority for International Application No. PCT/GB2014/051630.
(Continued)

*Primary Examiner* — Giovanni Astacio-Oquendo
*Assistant Examiner* — Alvaro Fortich
(74) *Attorney, Agent, or Firm* — Buchanan Ingersoll & Rooney PC (57) ABSTRACT

A glazing having a device for detecting a crack in the glazing comprises a sensor, substantially circumscribing a ply of glazing material. A surface contact, bonded to the glazing, is configured with a portion of the sensor to form a capacitive coupling for transferring AC signals in a frequency range. Preferably the sensor is frangible and voltage may be applied by a second surface contact. Alternatively, the glazing further comprises an electrically resistive element, such as a coating for heating the glazing, and voltage may be applied to the sensor by a spur from a busbar such that damage to coating, busbar or sensor resulting in arcing is detectable at the surface contact. An electronics module attached to the surface contact generates an alarm.

15 Claims, 6 Drawing Sheets

(51) Int. Cl.
*G08B 13/04* (2006.01)
*G01N 27/00* (2006.01)

(56) References Cited

U.S. PATENT DOCUMENTS

| | | | |
|---|---|---|---|
| 4,902,875 A | 2/1990 | Koontz | |
| 4,939,348 A | 7/1990 | Criss | |
| 5,145,744 A * | 9/1992 | Cartier | B32B 17/10018 |
| | | | 428/423.7 |
| 6,535,126 B2 * | 3/2003 | Lin | G08B 13/04 |
| | | | 340/545.4 |
| 2003/0127452 A1* | 7/2003 | Gerhardinger | A47F 3/0434 |
| | | | 219/497 |
| 2006/0018000 A1* | 1/2006 | Greer | G02F 1/163 |
| | | | 359/265 |
| 2009/0033123 A1 | 2/2009 | Torr et al. | |
| 2010/0060077 A1* | 3/2010 | Paulus | B32B 17/10036 |
| | | | 307/10.1 |
| 2010/0220019 A1 | 9/2010 | Boote | |
| 2010/0232677 A1* | 9/2010 | Bartsch | G01N 21/958 |
| | | | 382/141 |
| 2011/0187855 A1* | 8/2011 | Pichon | G01B 11/2513 |
| | | | 348/136 |
| 2012/0081226 A1 | 4/2012 | Hu | |
| 2012/0086614 A1 | 4/2012 | Droste et al. | |

FOREIGN PATENT DOCUMENTS

| | | |
|---|---|---|
| DE | 195 01 103 A1 | 7/1996 |
| DE | 202009018455 U1 | 12/2011 |
| EP | 0 430 119 A2 | 6/1991 |
| EP | 1 538 577 A2 | 6/2005 |
| EP | 1 648 200 A1 | 4/2006 |
| FR | 2 625 581 A1 | 7/1989 |
| GB | 2 190 877 A | 12/1987 |
| JP | H-6-87407 A | 3/1994 |
| JP | 2003-085660 A | 3/2003 |

OTHER PUBLICATIONS

Written Opinion (PCT/ISA/237) issued on Sep. 1, 2014, by the European Patent Office as the International Searching Authority for International Application No. PCT/GB2014/051630.

Patent Act 1977: Search Report Under Section 17 dated Nov. 14, 2013 issued in the corresponding UK Patent Applicaiton No. GB1309549.2 (1 page).

* cited by examiner

GLAZING

BACKGROUND OF THE INVENTION

The invention relates to a glazing comprising a means for detecting a crack in the glazing.

Glazing may be provided with electrical devices such as crack detection elements, heating elements and antennas. Crack detection elements perform a damage detection function and are connected to a crack detection module which generates an alarm.

Heating elements perform defogging and de-icing functions and may comprise a transparent electrically resistive coating connected to a power supply. Antennas perform the function of receiving or transmitting data by electromagnetic waves, for example AM/FM radio, TV and mobile telephones.

It is known to provide an automotive glazing comprising a frangible wire for crack detection positioned around a periphery, for example DE9303273U1 (Trebe). Such a car alarm is sensitive to breakage by an intruder, causing glazing rupture.

It is known to provide a crack detector comprising a glazing having a conductive wire, connected via a terminal to an oscillator. In JP2003085660 (Asahi/Shibata) a glazing breakage is detected as a change in resonant frequency of the oscillator.

It is known to provide an antenna on a glazing connected via connection points to an alarm evaluator for crack detection. In DE19501103 (Flachglas/Paulus) an antenna in the viewing area of an automotive glazing performs two functions: an antenna for an AM/FM amplifier and a crack detection element for an alarm evaluator. The alarm evaluator applies DC voltage or low-frequency single-phase AC voltage to the antenna and measures resistance of the antenna. To prevent undesirable mutual influencing of the two functions of the antenna, connection between the AM/FM amplifier and the antenna is via a capacitor.

Crack detectors may be divided into two categories: "all or nothing" electronics modules, which require substantially complete opening of a circuit, and "threshold" electronics modules, which respond to a change in resistance of a circuit. "All or nothing" electronics modules can be very much simpler, and therefore less expensive. GB2190877 (Glaverbel/Laurent) discloses a laminated glazing comprising unequally stressed plies of glazing material, so that cracks reliably propagate from side to side of the glazing causing rupture, to allow use of an "all or nothing" electronics module.

Cracks in an outer ply of a laminated heated coated windscreen not resulting in rupture may cause a discontinuity in a coating or a busbar. Arcing or non-uniform current distribution around such a discontinuity may cause a hotspot in a part of the glazing and ineffective heating in another part. A hotspot may cause the crack to propagate, affecting the safety function of the windscreen. A hotspot may cause a fire.

It is known to detect a crack by measuring voltage across a coating or resistance of a coating. For example, in U.S. Pat. No. 4,565,919 (Donnelly/Bitter) a coating voltage is monitored and in EP1648200 (Pilkington/Dixon) an electronics module repeatedly determines a is threshold resistance based on a plurality of previous coating resistance values.

It is known to measure resistance of a sensor wire, connected to a top busbar, for example U.S. Pat. No. 4,829,163 (GM/Rausch), U.S. Pat. No. 4,902,875 (PPG/Koontz) and JPH06087407 (Denso/Ito). In EP0430119 (PPG/Koontz) two sensor leads are connected to tabs at predetermined positions on a coating. Disadvantageously, preferred embodiments of these disclosures require five edge connectors.

U.S. Pat. No. 4,939,348 (PPG/Criss) discloses a sensor lead which encircles a periphery of a glazing. A power source voltage for a heating element on the glazing is also applied to the sensor lead, permitting a voltage change to be detected in the event of a crack at any edge portion of the glazing. An electronics module detects a break in the sensor lead and generates a signal. U.S. Pat. No. 4,939,348 requires four edge connectors.

It is an object of the present invention to provide a glazing comprising an alternative means for detecting a crack in the glazing.

SUMMARY OF THE INVENTION

According to a first aspect of the present invention, a glazing is provided comprising the features set out in claim 1 attached hereto.

The present invention offers an alternative means for detecting a crack in a glazing by providing a surface contact connected by capacitive coupling to a sensor such that a voltage modulated by damage to a ply of glazing material is detectable at the surface contact.

Damage to the ply of glazing material may result in a discontinuity in the sensor which modulates a voltage in the sensor.

Voltage in the sensor may be induced or applied. Induced voltages may be due to ambient AC signals. For example, the sensor may act as an antenna to radio frequency signals. The sensor may also have a voltage applied to it by a device on the glazing, for example a piezoelectric device or a photovoltaic device, which harvests energy from the environment and produces a DC or an AC voltage.

Applied voltages may be applied to one end of the sensor. The modulated voltage is detectable at the surface contact connected by capacitive coupling to the other end of the sensor. In the case of a DC voltage in a frangible sensor, when the sensor breaks a transient voltage may be detected via the capacitive coupling.

Damage to the ply of glazing material may result in a discontinuity in an electrically resistive element, resulting in arcing. Arcing may cause an induced voltage in the sensor. The induced voltage, modulated by the damage to the ply of glazing material, is detectable at the surface contact connected by capacitive coupling to the sensor. An induced voltage due to arcing may have a characteristic frequency. The characteristic frequency for arc detection may be in the region 1 MHz to 60 MHz, more preferably in the region 20 MHz to 50 MHz.

Voltages may be applied to the sensor from a busbar via a busbar extension. The applied voltage of the busbar extension modulated by arcing due to damage to the ply of glazing material is detectable at the surface contact connected by capacitive coupling to the sensor.

The invention provides a glazing with a crack detection function, having fewer edge connectors and a simpler electronics module than glazings of the prior art. In laminated glazing, conductors emerging at an edge between an interlayer and a ply of glazing material may be points of water ingress resulting in de-lamination, so it is advantageous to minimise the number of edge connectors.

The technical effect is achieved by providing a surface contact connected by capacitive coupling to the sensor and monitoring voltage modulations due to damage to the ply of glazing material detectable at the surface contact.

Surprisingly, a glazing with crack detection function is provided by means of a surface contact tuned to receive AC signals in a frequency range for sensing electrical discontinuity in electrical devices on the glazing.

A glazing is provided comprising a ply of glazing material having a surface, a sensor for sensing a voltage modulated by damage to the ply of glazing material, is substantially circumscribing the ply of glazing material and a surface contact bonded to the surface configured with a portion of the sensor to form a capacitive coupling for transferring AC signals in a frequency range.

Preferably the sensor is frangible and the voltage is induced by an ambient AC signal and modulation of the voltage occurs when damage to the ply of glazing material causes the sensor to break and reduce an amplitude of the ambient AC signal.

Alternatively, the sensor is frangible and the glazing further comprises a second surface contact bonded to the surface of the ply of glazing material, configured with a sensor portion to form a capacitive coupling for transferring AC signals in a frequency range and an AC voltage is applied to the sensor via the second surface contact.

Preferably modulation of the voltage occurs when damage to the ply of glazing material causes the sensor to break and arcing occurs adding a characteristic AC signal to the voltage.

Preferably the glazing further comprises an electrically resistive element on a surface of the ply of glazing material.

Preferably modulation of the voltage occurs when damage to the ply of glazing material causes arcing which induces a characteristic AC signal in the sensor.

Preferably the electrically resistive element is on an inner surface of the ply of glazing material.

Alternatively, the electrically resistive element is on an inner surface of an inner ply of glazing material.

Preferably the sensor comprises a sensor portion which is electrically connected to a busbar by a connecting section for applying a heater circuit voltage to the sensor and modulation of the heater circuit voltage occurs when damage to the ply of glazing material causes a discontinuity in the electrically resistive element, a busbar or the sensor resulting in arcing which adds a characteristic AC signal in the sensor.

Alternatively the glazing comprises a second surface contact bonded to the surface of the ply of glazing material configured with a sensor portion to form a capacitive coupling for transferring AC signals in a frequency range and an AC voltage is applied to the sensor via the second surface contact and modulation of the AC voltage occurs when damage to the ply of glazing material causes a discontinuity in the electrically resistive element, a busbar or the sensor resulting in arcing which adds a characteristic AC signal in the sensor (16).

Preferably the glazing further comprises an obscuration band on a surface of the ply of glazing material.

Preferably the surface contact further comprises an electronics module.

Preferably the sensor is configured in a periphery of the ply of glazing material.

Preferably the voltage modulated by damage to the ply of glazing material is in the range 0.1 MHz to 6 GHz.

According to the invention from a second aspect, a crack detector is provided comprising a glazing according to claim 1 and an electronics module, wherein the voltage modulated by damage to the ply of glazing material is detected at the surface contact by the electronics module and compared with at least one reference value.

BRIEF DESCRIPTION OF THE DRAWINGS

The invention will now be described by means of non-limiting examples with reference to the attached figures.

DETAILED DESCRIPTION OF THE INVENTION

Figure 1:
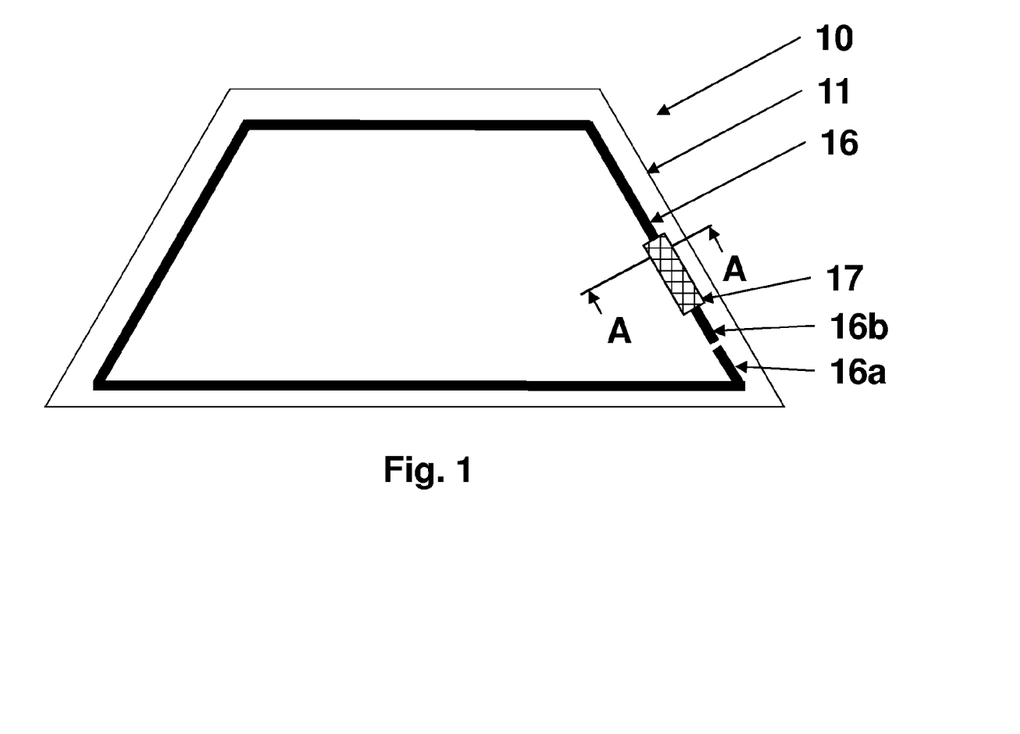
FIG. 1 shows a glazing according to the invention.

FIG. 1 shows a glazing 10 according to the invention. A windscreen is shown for ease of illustration of the invention but it will be understood by the reader that the invention is not limited to such windscreens and includes side window glazings, rear window glazings and roof window glazings.

The glazing 10 comprises a ply of glazing material 11. The ply of glazing material may be annealed glass. In an advantageous embodiment the ply of glazing material 11 is semi-toughened glass or toughened glass. Toughening provides two advantages. Firstly, increased surface strength of the ply of glazing material 11 results in reduced likelihood of damage. Secondly, if an impact exceeds the surface strength of the ply of glazing material 11 then a crack formed by the impact will propagate causing the glazing 10 to shatter. Thus the crack will propagate to a region where it may be detected.

A sensor 16 is arranged on a surface of the ply of glazing material 11. In an advantageous embodiment, the sensor 16 is arranged in a periphery of the ply of glazing material 11. The periphery is defined as less than 40 mm from an edge. A technical effect of arranging the sensor 16 in a periphery of the ply of glazing material 11 is that cracks originating in the periphery are detected immediately. A second technical effect is that the sensor 16 does not obscure a primary vision area of the glazing 10. By contrast, DE19501103 (Flachglas/Paulus) discloses an antenna at least 40 mm from an edge.

A surface contact 17 is arranged for capacitive coupling to the sensor 16. The surface contact 17 may be positioned adjacent to any portion 16b of the sensor 16. For is ease of illustration, the surface contact 17 and the portion 16b of the sensor 16 are shown as straight lines. The surface contact 17 and the portion 16b of the sensor 16 may have any shape and any length. Shapes and lengths are chosen to select a desired capacitance of the capacitive coupling formed by the surface contact 17 and the portion 16b of the sensor 16. An advantageous shape for the portion 16b of the sensor 16 is a linear conductor in a meander shape. An advantageous shape for the surface contact 17 is a rectangular pad.

It is known that a wavelength of electromagnetic radiation in air is related to a wavelength in a glazing 10 by a shortening factor. The shortening factor depends on relative permittivity of materials comprising the glazing 10 and a shape of a portion 16b of a sensor 16, arranged to conduct a corresponding AC signal in the glazing 10 and a shape of a surface contact 17, arranged to form a capacitive coupling with the portion 16b. Electromagnetic radiation, having wavelength in air of 6 meters, conducted by a folded portion 16b of a silver print sensor 16 on a ply of glass 11 and a pad shaped surface contact 17 may be subject to a shortening factor of 0.6. So an effective wavelength in the glazing 10 of a corresponding AC signal is 3.6 meters. A length of portion 16b is selected as 0.9 meters, a quarter of the effective wavelength. In an advantageous embodiment, the length of the portion 16b of the sensor is an odd multiple of a quarter of an effective wavelength in the glazing 10 such that the portion 16b of the sensor together with a surface contact 17 form a band-pass filter and voltages in a desired frequency band in the sensor 16 are detectable at the surface contact 17.

During operation, AC voltages induced in the sensor 16 by background electromagnetic radiation are detected at the surface contact 17. In the event of damage to the glazing and hence to the sensor 16, a noticeable change in amplitude, phase or frequency of electromagnetic radiation is detected at the surface contact 17 and is used to trigger an alarm. Methods of processing of voltages and algorithms to determine when to trigger an alarm are known to persons skilled in the art. The glazing 10 may be incorporated in a crack detector system, comprising an electronics module 20 in electrical contact with the surface contact 17. The electronics module 20 compares the induced voltages with at least one reference value. Such a reference value may be derived from a previous measurement of induced voltages. In its broadest sense, the invention senses change to any voltage that is modulated by damage to the glazing 10. Sensing change to any voltage means measuring potential difference between the surface contact 17 and a reference terminal. In the case of a crack detector system, the electronics module 20 comprises a reference terminal. In the case of a crack detector system installed in a vehicle, the reference terminal may be the vehicle body.

Figure 2:
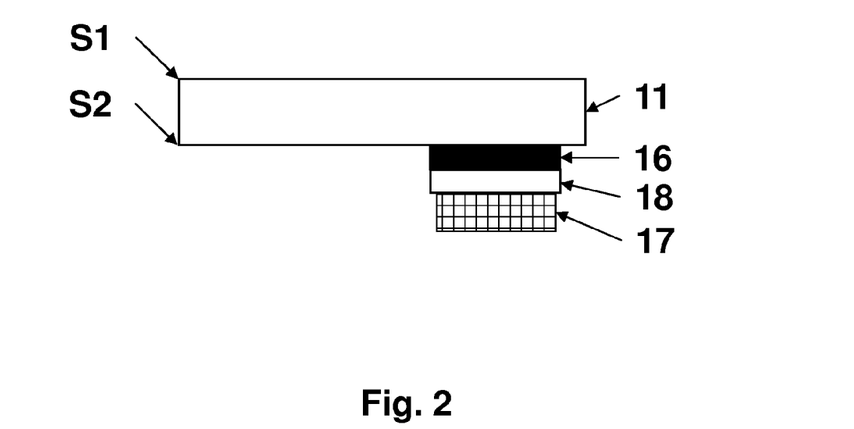
FIG. 2 shows a single-ply glazing according to the invention in cross-section.

FIG. 2 shows a single-ply glazing according to the invention in cross-section. In an advantageous embodiment, the surface contact 17 is attached to the glazing 10 by an electrically insulating adhesive layer 18. Thickness of the electrically insulating adhesive layer 18 may be selected to achieve a desired capacitance between the surface contact 17 and the portion 16b of the sensor. An advantageous thickness is less than 1 mm. An example of an electrically insulating adhesive layer 18 is a self-adhesive pad.

Figure 3:
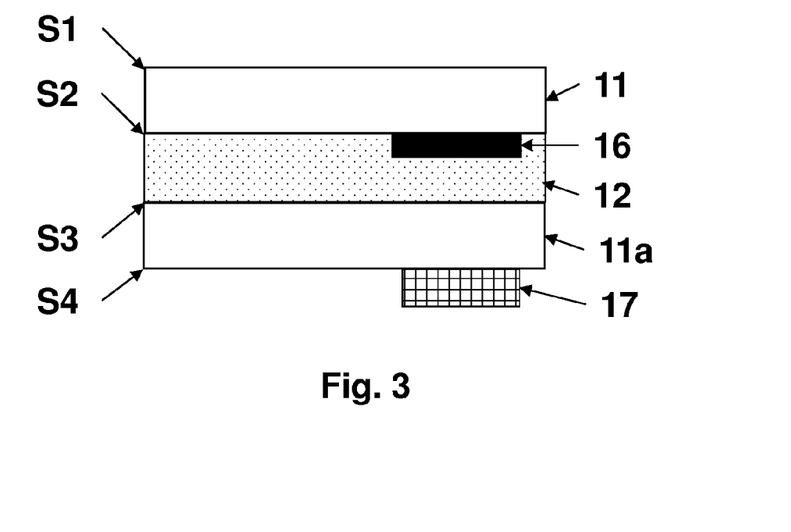
FIG. 3 shows a laminated glazing according to the invention in cross section.

FIG. 3 shows a laminated glazing according to the invention in cross section. A first ply of glazing material 11 has an outer surface S1 and an inner surface S2. A second ply of glazing material 11a has an inner surface S3 and an outer surface S4. In an advantageous embodiment, outer surface S1 faces an external environment and outer surface S4 faces in internal environment of a building or a vehicle. Between first and second plies of glazing material 11,11a is a ply of interlayer material 12. An example of a ply of an interlayer material 12 is polyvinyl butyral, PVB.

Figure 4:
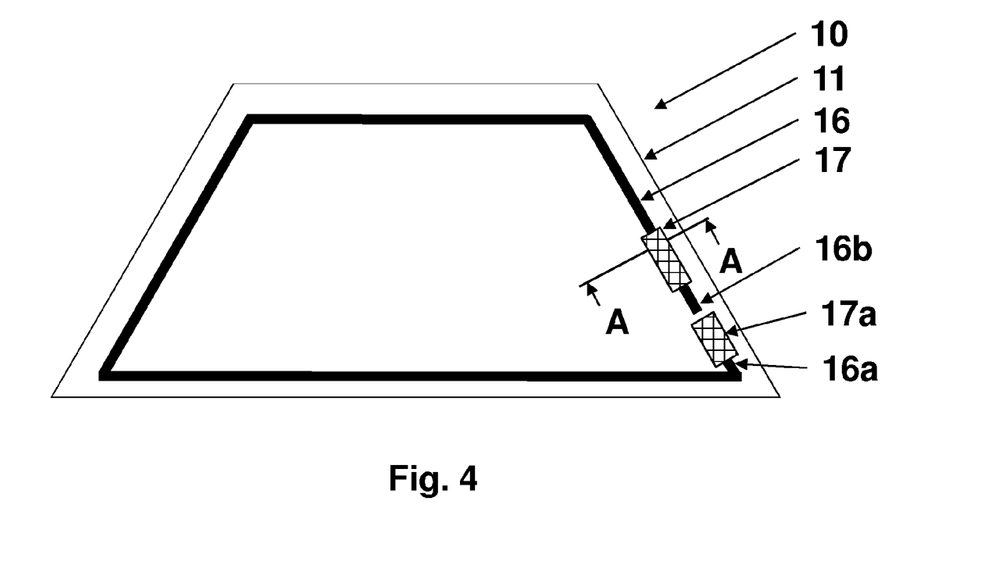
FIG. 4 shows a glazing according to the invention having a second surface contact.

FIG. 4 shows a glazing 10 according to the invention having a second surface contact 17a connected by capacitive coupling to a sensor portion 16a for transmitting a signal via the sensor 16. An applied voltage at sensor portion 16a is transmitted to the portion 16b of the sensor 16 connected by capacitive coupling to the surface contact 17. A crack in ply of glazing material 11 causing a discontinuity in the sensor 16 modulates the applied voltage and is detectable at the surface contact 17.

Figure 5:
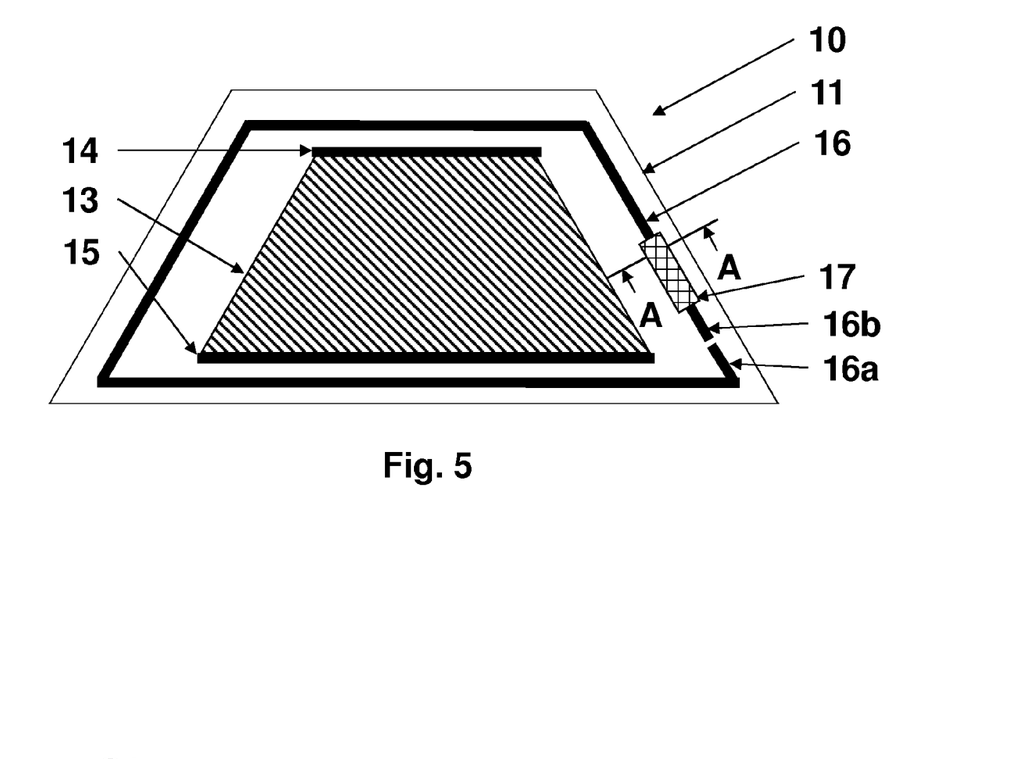
FIG. 5 shows a glazing according to the invention having an electrically resistive element.

FIG. 5 shows a glazing 10 according to the invention having an electrically resistive element 13. An example of an electrically resistive element is a coating of transparent conductive oxide. A further example is an array of fine wires. A power supply is connected to two busbars 14, 15. An example of busbar material is silver print ceramic frit. Such busbars are known to the skilled person.

Figure 6:
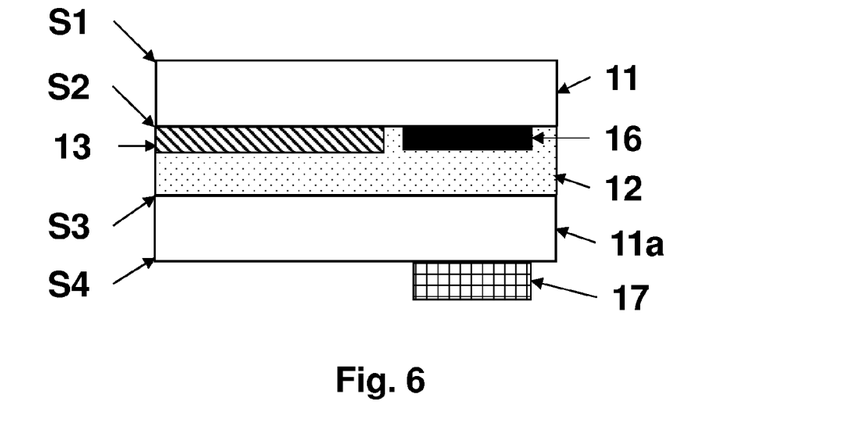
FIG. 6 shows a laminated glazing in cross section, sensor on S2 and element on S2.

FIG. 6 shows a laminated glazing 10 according to the invention in cross section, comprising a sensor 16 on a surface S2 of a ply of glazing material 11 and an electrically resistive element 13 on surface S2. The electrically resistive element 13 may be a coating applied to the ply of glazing material 11 or to the interlayer material 12. An example of such a coating is indium tin oxide, ITO. An advantage of the embodiment in which the first ply of glazing material 11 has the electrically resistive element 13 and the sensor 16 on it is that the glazing is easily shaped using the Pilkington Advanced Press Bending Process, which is known to the skilled person.

Figure 7:
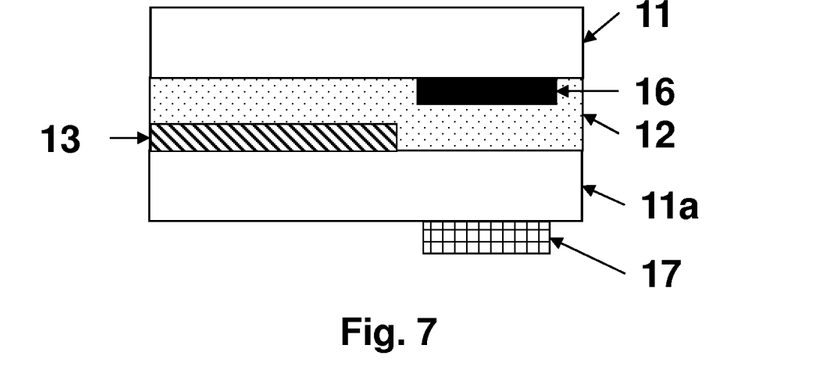
FIG. 7 shows a laminated glazing in cross section, sensor on S2 and element on S3.

FIG. 7 shows a laminated glazing 10 according to the invention in cross section, having a sensor 16 on a surface S2 of a first ply of glazing material 11 and an electrically resistive element 13 on surface S3 of a second ply of glazing material 11a. An advantage of this embodiment is that the sensor 16 comprising a frangible material may detect "false cracks", i.e. cracks in the first ply of glazing material 11 which do not affect the second ply of glazing material 11a and therefore do not affect the function of the electrically resistive element 13 on surface S3.

Figure 8:
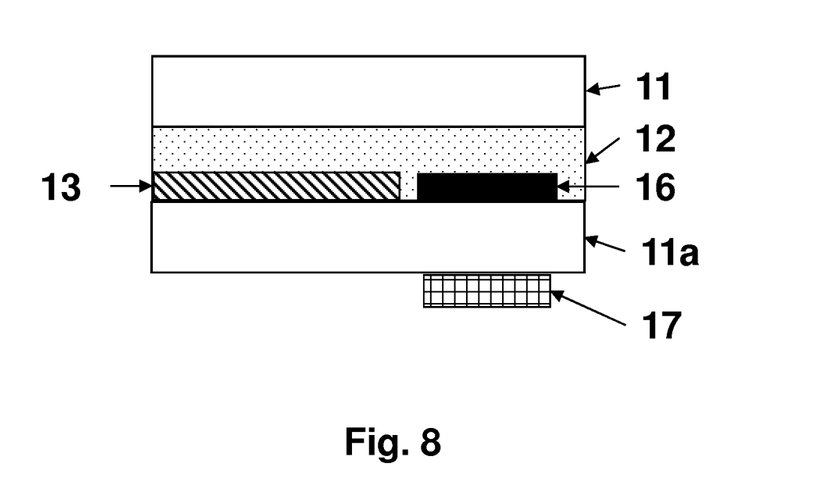
FIG. 8 shows a laminated glazing in cross section, sensor on S3 and element on S3.

FIG. 8 shows a laminated glazing 10 according to the invention in cross section, having a sensor 16 on S3 and electrically resistive element 13 on S3. An advantage of this embodiment is that both the sensor 16 and element 13 are mechanically shielded from impact of, for example, stones on surface S1 of a windshield and therefore are less likely to be damaged by a resulting crack.

Figure 9:
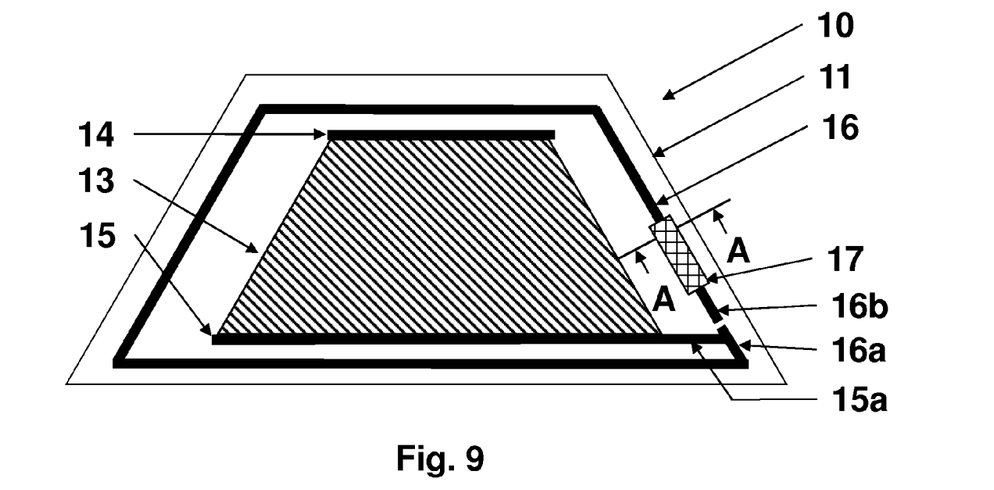
FIG. 9 shows a laminated glazing having sensor connected to busbar extension.

FIG. 9 shows a laminated glazing 10 having sensor 16 connected to busbar extension 15a. An advantage of this embodiment is that a voltage from busbar 15 is applied via busbar extension 15a to the sensor portion 16a. In the case of damage to the electrically resistive element 13 resulting in arcing, an AC voltage will be generated by the arcing and applied to a power supply voltage at busbar 15. The applied AC voltage will be transmitted as a signal via the sensor 16 to the surface contact 17.

Figure 10:
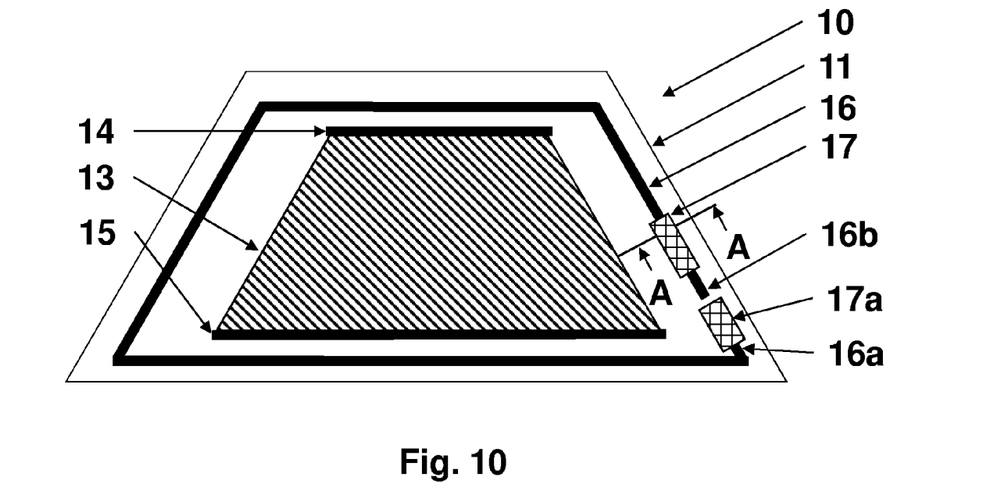
FIG. 10 shows a laminated glazing having an element and a second surface contact.

FIG. 10 shows a laminated glazing 10 having an electrically resistive element 13 and a second surface contact 17a. The second surface contact 17a forms a capacitive coupling with portion 16a of the sensor 16. This embodiment combines the advantages of embodiments of FIG. 4 and FIG. 5 such that discontinuity in the sensor 16 is detectable is as modulation of an applied voltage from the second surface contact 17a and discontinuity in the element 13 is detectable as modulation of an induced voltage due to arcing. Both modulations are detectable at the surface contact 17.

Figure 11:
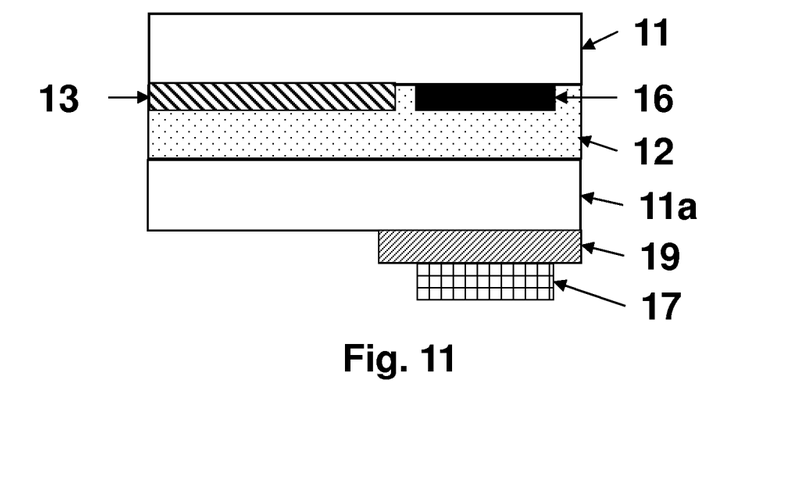
FIG. 11 shows a laminated glazing having an obscuration band.

FIG. 11 shows a laminated glazing 10 having an obscuration band 19. The obscuration band 19 is made of opaque material. This embodiment has the advantage that the sensor 16 is hidden when viewed from the interior of a vehicle.

Figure 12:
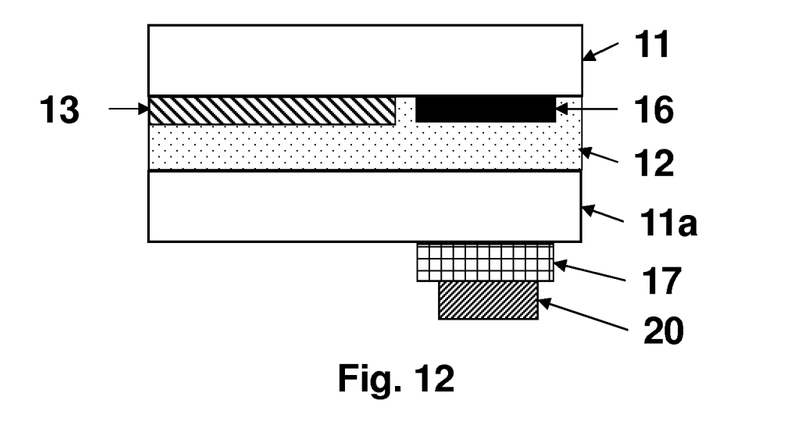
FIG. 12 shows a laminated glazing having an electronics module on the surface contact.

FIG. 12 shows a laminated glazing 10 having an electronics module 20 on the surface contact 17. This embodiment has the advantage that the electronics module is integrated in the glazing and therefore there is no need for an interconnecting cable. Thus small modulations of induced voltage or applied voltage may be detected reliably.

In a functional example, a laminated windshield 10 according to FIG. 9 has a sensor 16 connected via a spur 15a to a busbar 15 for an electrically resistive element 13; all electrical devices are on an inner surface S2 of the glazing 10. Damage to an outer surface S1 causes a crack which propagates to the inner surface S2 resulting in a discontinuity in the busbar 15. When a DC heating voltage is applied to the busbar 15, an arcing current in the range 40 A to 50 A flows across the discontinuity in the busbar 15 and generates an AC signal at a characteristic frequency. The AC signal is superposed on the DC heating voltage. The AC signal's characteristic frequency may be 50 MHz. It is known that a wavelength of electromagnetic radiation in air is related to a wavelength in the glazing 10 by shortening factors, which depend on permittivity of materials comprising the glazing 10, a shape of a portion 16b arranged to conduct the AC signal and a shape of a surface contact 17. In this example, the arcing current's wavelength in air is 6 meters and an effective wavelength in the glazing of the corresponding AC signal is 3.6 meters. A length of portion 16b is selected as 0.9 meters, a quarter of the effective wavelength. Advantageously, the length of portion 16b is selected so that, with surface contact 17, a capacitive coupling is formed. The capacitive coupling is thus tuned to sense arcing. An electronics module 20 bonded to the surface contact 17 compares the AC signal's amplitude with a reference and triggers an alarm if the reference is exceeded. When the glazing 10 is fitted in a vehicle, the electronic module 20 activates an alarm to alert a driver of the vehicle that a crack has been detected in the glazing 10.

The invention claimed is:

1. A glazing comprising:
   a ply of glazing material having a surface;
   a sensor for sensing a voltage modulated by damage to the ply of glazing material, said sensor at least partially circumscribing the ply of glazing material; and
   a surface contact bonded to the surface configured with a portion of the sensor to form a capacitive coupling for transferring AC signals, said surface contact being tuned to receive the AC signals in a frequency range for sensing electrical discontinuity in electrical devices on the glazing.

2. A glazing according to claim 1, wherein the sensor is frangible and the voltage is induced by an ambient AC signal and modulation of the voltage occurs when damage to the ply of glazing material causes the sensor to break and reduce an amplitude of the ambient AC signal.

3. A glazing according to claim 1, wherein the sensor is frangible and further comprising a second surface contact bonded to the surface of the ply of glazing material configured with a sensor portion to form a capacitive coupling for transferring AC signals in a frequency range and an AC voltage is applied to the sensor via the second surface contact.

4. A glazing according to claim 3, wherein modulation of the voltage occurs when damage to the ply of glazing material causes the sensor to break and arcing occurs adding a characteristic AC signal to the voltage.

5. A glazing according to claim 1, further comprising an electrically resistive element on a surface of the ply of glazing material.

6. A glazing according to claim 5, wherein modulation of the voltage occurs when damage to the ply of glazing material causes arcing which induces a characteristic AC signal in the sensor.

7. A glazing according to claim 5, wherein the electrically resistive element is on an inner surface of the ply of glazing material.

8. A glazing according to claim 5, wherein the electrically resistive element is on an inner surface of an inner ply of glazing material.

9. A glazing according to claim 5, wherein the sensor comprises a sensor portion which is electrically connected to a busbar by a connecting section for applying a heater circuit voltage to the sensor and modulation of the heater circuit voltage occurs when damage to the ply of glazing material causes a discontinuity in the electrically resistive element, the busbar or the sensor resulting in arcing which adds a characteristic AC signal in the sensor.

10. A glazing according to claim 5, further comprising a second surface contact bonded to the surface of the ply of glazing material configured with a sensor portion to form a capacitive coupling for transferring AC signals in a frequency range and an AC voltage is applied to the sensor via the second surface contact and modulation of the AC voltage occurs when damage to the ply of glazing material causes a discontinuity in the electrically resistive element, a busbar or the sensor resulting in arcing which adds a characteristic AC signal in the sensor.

11. A glazing according to claim 1, further comprising an obscuration band on a surface of the ply of glazing material.

12. A glazing according to claim 1, wherein the surface contact further comprises an electronics module.

13. A glazing according to claim 1, wherein the sensor is configured in a periphery of the ply of glazing material.

14. A glazing according to claim 1, wherein the voltage modulated by damage to the ply of glazing material is in the range 0.1 MHz to 6 GHz.

15. A crack detector comprising:
   a glazing comprising a ply of glazing material having a surface, a sensor for sensing a voltage modulated by damage to the ply of glazing material, said sensor at least partially circumscribing the ply of glazing material, and a surface contact bonded to the surface configured with a portion of the sensor to form a capacitive coupling for transferring AC signals, said surface contact being tuned to receive the AC signals in a frequency range for sensing electrical discontinuity in electrical devices on the glazing; and
   an electronics module, wherein the voltage modulated by damage to the ply of glazing material is detected at the surface contact by the electronics module and compared with at least one reference value.

* * * * *